United States Patent
Karsten

(10) Patent No.: US 6,713,165 B1
(45) Date of Patent: Mar. 30, 2004

(54) MULTILAYER THERMOPLASTIC STRUCTURE

(75) Inventor: Petrus J. A. Karsten, Havikshoek (NL)

(73) Assignee: Solvay (Societe Anonyme), Brussels (BE)

( * ) Notice: Subject to any disclaimer, the term of this patent is extended or adjusted under 35 U.S.C. 154(b) by 0 days.

(21) Appl. No.: 09/958,355

(22) PCT Filed: Mar. 29, 2000

(86) PCT No.: PCT/EP00/02759

§ 371 (c)(1),
(2), (4) Date: Jul. 16, 2002

(87) PCT Pub. No.: WO00/61062

PCT Pub. Date: Oct. 19, 2000

(30) Foreign Application Priority Data

Apr. 8, 1999 (BE) .............................. 9900244

(51) Int. Cl.⁷ ............................. B32B 7/02; B32B 27/32
(52) U.S. Cl. ............. 428/213; 264/173.14; 264/173.15; 428/220; 428/515; 428/516; 428/517; 428/519; 428/520; 428/910
(58) Field of Search ................................. 428/213, 220, 428/219, 515, 516, 517, 519, 520, 910, 35.2; 264/173.12, 173.14, 173.15

(56) References Cited

U.S. PATENT DOCUMENTS

| | | |
|---|---|---|
| 4,775,562 A | 10/1988 | Shishido et al. |
| 4,828,892 A | 5/1989 | Kersten et al. |
| 4,929,479 A | 5/1990 | Shishido et al. |
| 5,817,395 A | 10/1998 | Karsten et al. |
| 5,962,092 A * | 10/1999 | Kuo et al. .................. 428/34.9 |
| 6,127,043 A | 10/2000 | Lange |
| 6,174,479 B1 | 1/2001 | Gilliard et al. |

* cited by examiner

*Primary Examiner*—D. S. Nakarani
(74) *Attorney, Agent, or Firm*—Stites & Harbison PLLC; B. Aaron Schulman

(57) ABSTRACT

Multilayer structure based on thermoplastic polymers which is substantially devoid of vinyl chloride polymers and of plasticizers of low molecular mass and which comprises at least 3 layers:

a first layer (A) comprising at least 60% by weight of at least one polyolefin of controllable crystallinity defined as comprising at least 90% of ethylene, of propylene or of butene and as having a softening temperature of less than 121° C., the thickness of the first layer being at least 20% of the total thickness of the structure and the first layer having a modulus of elasticity of less than 350 MPa;

a second layer (B), positioned between the first layer (A) and the third layer (C), comprising at least 40% by weight of at least one polyolefin of controllable crystallinity, the second layer having an overall softening temperature of less than 121° C.;

a third layer (C) comprising at least 50% by weight of at least one polyolefin of controllable crystallinity, the thickness of the third layer being from 5 to 30% of the total thickness of the structure and the third layer having a modulus of elasticity which is less than that of the first layer.

17 Claims, No Drawings

MULTILAYER THERMOPLASTIC STRUCTURE

The present invention relates to a multilayer structure based on a thermoplastic material, such as a tube or a film, which can be used in particular in the manufacture of articles for medical applications.

Articles intended for medical applications must meet not only conventional requirements, such as good mechanical strength or low cost, but also requirements—extremely strict—peculiar to this specific field of application, such as, for example, requirements relating to the biocompatibility properties of the said articles, their ability to be subjected to a sterilization treatment, their flexibility, their transparency, their weldability, their impact strength (including as regards containers filled with liquid) or the amount of extractable substances (for example, with hexane).

Until now, commercially available articles for medical use, for example infusion or blood bags, have been based on vinyl chloride polymers, for example on PVC. Although having several advantages, this type of polymer, however, has certain disadvantages, such as the need to incorporate high amounts of stabilizers in it for the purpose of improving its thermal stability or to incorporate high amounts of plasticizers in it for the purpose of obtaining sufficient flexibility. There is therefore a market demand for articles for medical applications which are devoid of chlorinated polymers.

Polyolefin-based articles of this type have already been provided. Thus, for example, International Patent Application WO 97/34951 (Sengewald) discloses multilayer polyolefin-based films which can be used in particular in medical applications.

Known copolymer-based articles exhibit, however, the frequent disadvantage of comprising a significant amount of copolymer(s) with a high content of comonomer, which certainly increases their flexibility but reduces their melting temperature, which is a disadvantage with regard to the dimensional stability of the articles during steam sterilization (121° C.), and often results in a high content of extractable constituents. In addition, the transparency of these articles is often mediocre because of the rapid crystallization of the polyolefins generally used.

Furthermore, the known articles based on propylene homopolymers often comprise polymers of low isotacticity, which certainly makes it possible to obtain good flexibility but results in a high content of extractable constituents. In addition, they often exhibit a high polydispersity, which means that their melting temperature ranges and crystallization temperature ranges widely overlap, which makes it impossible to effectively reduce the crystallinity and to obtain good transparency.

For the purpose of overcoming these disadvantages, the present invention relates to a multilayer structure based on thermoplastic polymers which is substantially devoid of vinyl chloride polymers and of plasticizers of low molecular mass and which comprises at least 3 layers:

a first layer (A) comprising at least 60% by weight of at least one polyolefin of controllable crystallinity defined as comprising at least 90% of ethylene, of propylene or of butene and as having a softening temperature of less than 121° C., the thickness of the first layer being at least 20% of the total thickness of the structure and the first layer having a modulus of elasticity of less than 350 MPa;

a second layer (B), positioned between the first layer (A) and the third layer (C), comprising at least 40% by weight of at least one polyolefin of controllable crystallinity, the second layer having an overall softening temperature of less than 121° C.;

a third layer (C) comprising at least 50% by weight of at least one polyolefin of controllable crystallinity, the thickness of the third layer being from 5 to 30% of the total thickness of the structure and the third layer having a modulus of elasticity which is less than that of the first layer.

The term "multilayer structure" is understood to denote any multilayer semi-finished product and more particularly any film, sheet, tube or container.

An important constituent of the multilayer structure of the invention, present in each of the three layers A, B and C, is a polyolefin of controllable crystallinity. This expression denotes, in the context of the present invention, a polyolefin comprising at least 90% of ethylene, of propylene or of butene which has a softening temperature (a "Vicat point") of less than 121° C. (in the present application, all the softening temperatures are measured according to ASTM Standard D1525). The softening temperature in question relates to the polyolefin of controllable crystallinity as present in the structure of the invention. In particular, it is possible to use a polyolefin with a softening temperature, indicated by the manufacturer, of greater than 121° C. by choosing the conditions for the manufacture of the structure so that the true softening temperature of the said polyolefin within the said structure is less than 121° C. The polyolefins of this type exhibit the distinguishing feature that their crystallinity can be easily reduced during their processing. The "polyolefins of controllable crystallinity" advantageously exhibit a relaxation time $\tau_0$ of at least 10 s (and preferably of at least 15 s) at the extrusion temperature ($T_0$) and in the absence of any drawing stress.

This ready control of the crystallinity is advantageous in the content of the invention, in so far as it makes it possible to confer a reduced crystallinity on these polyolefins, provided that appropriate processing conditions are used, thus increasing the transparency and the flexibility of the whole structure. It is for this reason that the polyolefins are described as "polyolefins of controllable crystallinity".

Several such polyolefins can be used as a mixture, whether in one or more of the layers A, B and C, the minimum amount indicated hereinabove relating, in this case, to the sum of the amounts of each of these polyolefins. An advantageous alternative form consists in using a mixture of polypropylene and of isobutene in a ratio from 1:3 to 3:1. The polyolefins of controllable crystallinity present in the layers A, B and C can be identical or different.

This polyolefin of controllable crystallinity can be a homopolymer of ethylene, of propylene or of butene. Mention may be made, as non-limiting examples of such homopolymers, of propylene homopolymers (PP) [including syndiotactic PPs (s-PP), stereo-block PPs (s-b-PP) or iso-block PPs (i-b-PP)] or poly(1-butene). The preferred homopolymers are syndiotactic, stereo-block and iso-block polypropylenes and poly(1-butene).

It is preferable for the polyolefin of controllable crystallinity to be a copolymer. It can in particular be a copolymer of several of these three monomers (ethylene, propylene, butene) comprising at least 90% of one of these monomers and less than 10% of one or each of the other two monomers. According to another alternative form, the polyolefin of controllable crystallinity is a copolymer comprising at least 90% by weight of ethylene, of propylene or of butene and less than 10% of one or more other comonomers chosen from the group composed of $C_5$ to $C_{10}$ hydrocarbons, carboxylic acids and their esters and carbon monoxide (examples: 1-pentene, 1-hexene, 1-octene, 4-methyl-1-pentene, vinyl acetate, methyl, ethyl or butyl acrylate, cyclohexene, norbornene, and the like). Mention may be made, as non-limiting examples of such copolymers, of low density polyethylenes (LLDPE, VLDPE) and copolymers of ethylene with other α-olefins (such as 1-butene, 1-hexene, 1-octene, 4-methyl-1-pentene or 1-pentene) or with compounds such as vinyl acetate, acrylic acid or methyl, ethyl or butyl acrylate (provided that these copolymers exhibit a content of comonomer(s) of less than 10%).

It should be noted that, in the present application, in the absence of contrary indications, the term "copolymers" encompasses polymers comprising two or more comonomers.

As regards the copolymers, the amount of the minor comonomer(s) is preferably at least 1.5% by weight. In particular, it is preferable to use, as polyolefin of controllable crystallinity, a copolymer comprising at least 90% by weight of propylene and at least 2% by weight of ethylene and/or of butene.

As regards the homopolymers and the copolymers, their polydispersity is advantageously less than 8 and preferably less than 4. This characteristic reflects a low dispersion of the molecular masses, which increases the separation between the melting temperature ranges and softening temperature ranges and thus makes it possible to have a more effective action on the crystallinity during the processing.

Furthermore, the melt flow index of the polyolefin of controllable crystallinity used is advantageously less than 10 g/10 min, preferably less than 5 g/10 min (measured according to ASTM Standard D1238, under the conditions 190° C./2.16 kg for the polymers of ethylene and the copolymers of butene and under the conditions 230° C./2.16 kg for the polymers of propylene and the homopolymers of butene).

Preferably, at least one polyolefin of controllable crystallinity in the first layer (A) exhibits a melting temperature of greater than 121° C. and more preferably of greater than 130° C. Advantageously, at least one polyolefin of controllable crystallinity in the third layer (C) exhibits a melting temperature of greater than 121° C. and more preferably of greater than 130° C. It is preferably the same for at least one polyolefin of controllable crystallinity in the second layer (B). This characteristic is advantageous. for the purpose of steam sterilization (at 121° C.).

In addition to one or more polyolefins of controllable crystallinity as described hereinabove, the layers A, B and C can optionally comprise one or more other thermoplastic polymers. These other polymers are advantageously chosen from not very crystalline or amorphous polyolefins of the following types:

olefinic copolymers composed of at least two $C_2$ to $C_{10}$ alkenes, comprising at least 60% by weight of ethylene and/or of propylene and/or of butene but not comprising more than 90% by weight of the same comonomer, or from olefinic copolymers comprising ethylene and/or propylene and/or butene and from 10 to 40% by weight of one or more different comonomers (which are preferably chosen from $C_5$ to $C_{10}$ olefins and carboxylic acid or ester groups, for example vinyl acetate, methyl, ethyl or butyl acrylate and methyl methacrylate, or carbon monoxide), or from elastomeric copolymers with blocks of styrene and of an olefin (for example, copolymers of the styrene-butadiene-styrene or styrene-ethylene-propylene-styrene type, and the like), or from highly branched homopolymers [for example, low density polyethylene (LDPE) or medium density polyethylene (MDPE)], and finally from cycloolefin copolymers (COC), such as norbornene-based copolymers, for example.

The term "COC" is understood to mean copolymers based on a $C_2$ to $C_{10}$ olefin and on a $C_5$ to $C_{16}$ cyclic monomer in a respective content of 20 to 98% by weight for the olefin and of 2 to 80% by weight for the cyclic monomer. The olefin is advantageously ethylene. The cyclic monomer can be cyclopentene, cyclohexene, dicyclopentadiene, tetracyclododecene or methyltetra-cyclododecene. The COC is preferably a copolymer of ethylene and norbornene. In this case, the content of ethylene is advantageously between 30 and 80% by weight and the content of norbornene between 20 and 70%.

Examples of not very crystalline or amorphous polyolefins which can be used are ethylene-vinyl acetate (EVA), ethylene-methyl acrylate (EMA), ethylene-ethyl acrylate (EEA) or ethylene-butyl acrylate (EBA) copolymers, low density ethylene copolymers (LLDPE, VLDPE, ULDPE), polyolefin elastomers (POE) and cycloolefin copolymers (COC). Among the abovementioned copolymers, only those which exhibit a content of comonomer(s) of at least 10% naturally come into consideration as additional constituents.

According to a preferred alternative form, the constituent polymer(s) of the layer A are chosen exclusively from the group consisting of polyolefins of controllable crystallinity and of not very crystalline or amorphous polyolefins as described hereinabove. This advantageous alternative form also relates to the layers B and C, independently of one another and independently of the layer A.

According to advantageous alternative forms of the invention, the layers A, B and C exhibit more specific properties described hereinbelow.

According to an advantageous alternative form, the layer A, taken as a whole, exhibits a melting temperature of greater than 121° C. Preferably, at least one polyolefin of controllable crystallinity included in the layer A exhibits a melt flow index (measured under the conditions mentioned hereinabove) of less than 10 g/10 min. Preferably, the modulus of elasticity of the layer A does not exceed 350 MPa (in the present application, all the moduli of elasticity are measured according to ASTM Standard D882).

According to an advantageous alternative form, the layer B, taken as a whole, exhibits a melting temperature of greater than 121° C. Preferably, its modulus of elasticity is less than 275 MPa and more particularly than 150 MPa. Furthermore, it is preferable for the thickness of the layer B to be from 20 to 70% of the total thickness of the structure.

According to an advantageous alternative form, the layer C, taken as a whole, exhibits a melting temperature of greater than 121° C. However, it is advantageous, while observing this condition, for the layer C to comprise at least one polymer with a melting temperature of less than 121° C., this being in order to improve the weldability of the structure. The amount of this or these polymer(s) is preferably from 1 to 10% of the weight of the layer C, indeed even from 2.5 to 7.5%. This or these polymer(s) can be chosen from polyolefins of controllable crystallinity and not very crystalline or amorphous polyolefins. They are preferably ethylene-vinyl acetate (EVA), ethylene-methyl acrylate (EMA), ethylene-ethyl acrylate (EEA) or ethylene-butyl acrylate (EBA) copolymers or low density ethylene copolymers (LLDPE, VLDPE, ULDPE). These polymers preferably exhibit a melting temperature of 70 to 105° C. approximately. These polymers are advantageously chosen so that they are only very slightly miscible or immiscible with the other ingredients of the layer C. Furthermore, the modulus of elasticity of the layer C is preferably less than 275 MPa.

According to a preferred alternative form, the layer A exhibits a modulus of elasticity which is greater than that of the layer B and than that of the layer C. According to an advantageous alternative form, the layer A exhibits a softening temperature which is greater than that of the layer B and than that of the layer C. According to a preferred alternative form, the layer A exhibits a melting temperature which is greater than that of the layer B and than that of the layer C.

The content of extractable aluminium in the structure is preferably less than 1 ppm (according to the European Pharmacopoeia).

It proved to be advantageous for the structure, taken as a whole, to exhibit a density of less than 0.905 kg/dm$^3$. In addition, it is preferable to use the alternative forms in which the embrittlement temperature (as defined by DIN Standard 53372) is at most 4° C.

In an advantageous alternative form, the ratio [tensile strength/yield strength] is greater than 1.5 (measured according to ASTM Standard D882) and preferably greater than 2.

Plasticizers of low molecular mass (Mw<1000) are substantially excluded from the multilayer stucture of the invention. This relates in particular to monomeric plasticizers, such as, for example, those based on phthalates. The characteristic according to which the structure of the invention is "substantially devoid" of vinyl chloride polymers and of plasticizers of low molecular mass means that possible constituents of this type, if they are present, are present in proportions not exceeding 0.1% by weight. Preferably, these compounds are completely absent from the structure.

The multilayer structure comprises at least the three layers A/B/C mentioned above, in this order, and optionally one or more other thermoplastic layers. The fact that the layer B is situated "between" the layers A and C does not mean that it is necessarily in contact with the latter; this is because one or more intermediate layers can be inserted between the layer B, on the one hand, and the layer A and/or C, on the other hand.

It is possible in particular to add, as intermediate layer, a layer corresponding to the same definition as the layer A, B or C which are described hereinabove. A particularly advantageous alternative form of this type is a 4-layer structure of A/C'/B/C type, in which the layer C' corresponds to the definition of the layer C given hereinabove. It is also possible to add one or more intermediate layers based on one or more thermoplastic polymers of any type but which is/are preferably chosen from polymers of the polyolefin-ketone (POK) type, cycloolefin copolymers (COC), polyisobutylene (PIB) or elastomeric polyesters, such as block copolymers based on carboxylic acid, on cylcoalkane and on diols (PCCE, and the like). In some applications, it can in addition be advantageous to provide a barrier layer, composed, for example, of an ethylene-vinyl alcohol ((EVOH) copolymer or of a polyamide (PA). If one or more intermediate layers are added between the layer A and the layer B, it is preferable for their cumulative thickness not to exceed 30% of the total thickness of the structure. The same applies to one or more possible intermediate layers which would be added between the layer C and the layer B. It is also possible to choose, as intermediate layer, a layer comprising recycled material based on structures according to the present invention.

Likewise, one or more outer layers based on thermoplastic polymer(s) can be added on the side of the layer A and/or of the layer C opposite the layer B. Thus, for example, the following structures can correspond to the definition of the invention: D/A/B/C; A/B/E/C; D/A/B/E/F/C or D/A/E/B/E/C/D/F. The optional outer layer(s) are based on one or more thermoplastic polymers of any type but which is/are preferably chosen from propylene homopolymers and from polymers of the following types: EVOH, POK, poly (ethylene tere-phthalate) PET, polycarbonate, polyamide (in particular PA-11 and/or PA-12) and cycloolefin copolymers (COC) Excellent results have been obtained with structures comprising a layer of POK or of polyamide next to the layer A (but, however, being able to be separated from the latter by a layer of adhesive).

Good results have also been obtained when the surface layer on the side of the layer A comprises COC (optionally as a mixture with SEBS and VLDPE) and/or PP homopolymer mixed with SEBS. This surface layer can, according to the situation, be the layer A itself or a layer external to the latter. The choice of such as surface layer makes it possible to prevent the structures according to the present invention from adhering to one another and/or to a possible packaging material, for example based on polyolefins (such as mixtures of PE and of isobutene).

If one or more outer layers are added to the structure on the outer side of the layer A (that is to say, on the side opposite the layer B), it is preferable for their cumulative thickness not to exceed 25% of the total thickness of the structure. The same applies to one or more optional outer layers added to the structure on the outer side of the layer C.

It is obvious that all the layers of the structure must be devoid of vinyl chloride polymers and of plasticizers of low molecular mass.

If necessary, a layer of adhesive can be inserted between two neighbouring layers. Any known adhesive can be used; use is preferably made, as adhesives, of a polyolefin grafted or modified by an anhydride, an acrylate, acrylic acid, a glycidyl compound or carbon monoxide, or a mixture of one or more such compounds with conventional polymers, such as a polyolefin or a polyester.

In addition, it is preferable for the overall modulus of elasticity of the structure not to exceed 500 MPa, preferably 350 MPa, in a particularly preferred way 200 MPa.

Although the structures according to the invention can have any thickness, their thickness is generally low, for example of the order of a millimeter for sheets and tubes and of the order of 100 to 300 µm for films, including containers composed of one or two films welded around their edge. According to an advantageous alternative form of the invention, the structure has a thickness not exceeding 400 µm and more preferably 300 µm.

The various characteristics described hereinabove make it possible to obtain particularly transparent structures. Their haze/thickness ratio is preferably less than 10%/200 µm and in a particularly preferred way less than 6%/200 µm, the (optical) haze being measured here according to the ASTM Standard D1003. For this measurement, in the case where the structure would be embossed on one or both of its faces (that is to say, would exhibit є roughness—Ra parameter, measured according to DIN Standard 4768—of greater than 0.5 µm overall or over part of this or these faces), it would be necessary to wet the structure by means of water and to trap it between two perfectly smooth and transparent glass plates. This ratio naturally only has meaning for thin structures having a thickness not exceeding approximately 500 µm. According to another preferred alternative form relating to the transparency, the structure of the invention preferably exhibits a light permeability (as defined by ASTM Standard D1003) of at least 95%.

A particularly important advantage of the structures of the invention is that they are capable of meeting the requirements of the European Pharmacopoeia (European Pharmacopoeia, version 3.1.6., supplement 1999) and of the United States standards (USP 32, 1995 for Class VI plastics-121° C.).

Other advantages of the structures of the invention are as follows:

- low initiation temperature for the sealing (approximately 125° C.) and broad sealing range (at least 15° C.);
- small amounts of compounds which can be extracted with boiling hexane (at reflux) (less than 5% by weight, indeed even less than 1%);
- water vapour transmission coefficient (ASTM Standard F1249) of less than 4 g/m²/day (at 23° C.);
- bags, the wall of which is a structure according to the invention, having a volume of one liter, filled with water at room temperature, withstand being dropped from 2 meters onto a flat surface.

In view of these noteworthy properties, the invention also relates to a multilayer structure based on thermoplastic polymers which are substantially devoid of vinyl chloride polymers and of plasticizers of low molecular mass, which comprises at least 3 layers and which has a total thickness of between 100 and 400 μm, the said structure simultaneously exhibiting:

- a modulus of elasticity of less than 350 MPa,
- an amount of compounds which can be extracted with boiling hexane of less than 5%,
- a haze/thickness ratio of less than 6%/200 μm.

On the basis of the preceding information, the manufacture of the structures of the invention is within the scope of a person skilled in the art. These structures can be manufactured in particular by coextrusion.

Preferably, for the purpose of reducing the crystallinity of a polyolefin of controllable crystallinity included in the structure, the process for the manufacture of the structure comprises at least one drawing stage, which takes place at a temperature between the crystallization temperature (Tc) of the polyolefin and Tm+15° C., Tm denoting its melting temperature, one relaxation stage, which takes place in the same temperature range, and one sudden cooling stage. Further details relating to such a process for modifying the crystallinity are provided in Patent Application EP 832,730 (Solvay).

Consequently, another subject-matter of the present invention is a process for the manufacture of a multilayer structure based on thermoplastic polymers which is substantially devoid of vinyl chloride polymers and of plasticizers of low molecular mass and which comprises at least 3 layers:

- a first layer (A) comprising at least 60% by weight of at least one polyolefin of controllable crystallinity defined as comprising at least 90% of ethylene, of propylene or of butene and as having a softening temperature of less than 121° C., the thickness of the first layer being at least 20% of the total thickness of the structure and the first layer having a modulus of elasticity of less than 350 MPa;
- a second layer (B), positioned between the first layer (A) and the third layer (C), comprising at least 40% by weight of at least one polyolefin of controllable crystallinity, the second layer having an overall softening temperature of less than 121° C.;
- a third layer (C) comprising at least 50% by weight of at least one polyolefin of controllable crystallinity, the thickness of the third layer being from 5 to 30% of the total thickness of the structure and the third layer having a modulus of elasticity which is less than that of the first layer;

according to which the various layers of the structure are coextruded and are then subjected:

- to at least one stage of drawing by at least 100%, which takes place at a temperature between the maximum crystallization temperature of the polyolefins of controllable crystallinity (Tc) and Tm+15° C., Tm denoting their minimum melting temperature, and
- to at least one stage of relaxation at constant dimensions lasting at least 10 s, which takes place in the same temperature range, then
- to a stage of sudden cooling to a temperature of less than the maximum crystallization temperature Tc.

The preferences indicated hereinabove with respect to the structure proper also apply as regards the process.

The maximum crystallization temperature of the polyolefins of controllable crystallinity is defined as being the highest of the crystallization temperatures of the polyolefins of controllable crystallinity present in the layers A, B and C. Their minimum melting temperature is defined as being the lowest of the melting temperatures of the polyolefins of controllable crystallinity present in the layers A, B and C.

The conditions of the drawing are advantageously such that the rate gradient is at least $1/(20 \times \tau_0)$ and preferably at least $1/(10 \times \tau_0)$, where $\tau_0$ denotes the mean relaxation time as defined hereinabove. The drawing stage causes monoaxial or biaxial drawing by at least 100% and preferably by at least 300%.

The relaxation is carried out at constant dimensions and in the absence of any external constraint. It is preferably carried out at the surface of a roller, maintained at the appropriate temperature, with which the structure comes into contact after it has been drawn.

According to an advantageous alternative form, several relaxation stages are separated by several drawing stages, the abovementioned draw ratio and the abovementioned relaxation time being overall values. This alternative form can be carried out by using several rollers rotating at different speeds.

The sudden cooling contributes to the increase in the transparency and the flexibility of the structure. It is preferably carried out at a temperature of less than Tc−50° C. This cooling can be carried out in particular by passing the structure into a thermostatically-controlled water bath or over a cooled roller; simple cooling with air is not sufficiently effective. Extrusion blow-moulding processes are consequently poorly suited.

Optionally, one or each of the faces of the structure of the invention can be embossed, that is to say furnished with a relief exhibiting a roughness (Ra) of more than 0.5 μm. It is advantageous, for the purpose of embossing the two faces of the structure, to use two, very hard, metal embossing rollers which simultaneously (and not sequentially) emboss the two faces of the structure over at least a portion of their surfaces (this being because it is possible for non-embossed "windows" to be provided on one or each of the faces). Further details with regard to this process are provided in Patent Application EP 743,163 (Solvay). This optional embossing stage preferably takes place between the drawing stage and the relaxation stage.

The structures described hereinabove are particularly advantageous when they are used in the medical field, for example in the preparation of films, sheets, tubes, containers or similar articles intended to come into contact with biological tissues or with biological or medicinal fluids, such as blood or infusion solutions. In particular, the invention also relates to a structure as defined hereinabove which is provided in the form of a tube, of a film or of a container. More particularly, it also relates to a flexible bag obtained from two films as described hereinabove which are welded around their edge or alternatively from a tubular film which is welded around its edge, so as to obtain a hermetic container (equipped, however, with appropriate pipes allowing it to be filled and emptied).

The structure forming the subject-matter of the invention is intended in particular to be used so that it is the layer C which comes into contact with biological tissues or biological or medicinal fluids. Consequently, the invention relates in particular to a tube or a container prepared by means of the abovementioned structure, the layer C of which is facing inwards. The layer C preferably constitutes the inner surface layer of the said tube or container.

The structure can naturally be advantageously used in other applications, for example in the packaging or the transportation of fluids of any type, for example foodstuffs, such as drinks, jam, and the like.

In the case where the layer C, taken as a whole, exhibits a melting temperature of greater than 121° C. but nevertheless comprises at least one polymer with a melting temperature of less than 121° C., the structure according to the present invention can be welded to itself or to another structure having an outer layer with the same composition as the layer C (the layer C acting as sealing layer), so as to obtain a weld with a reproducible peel strength.

Consequently, the present invention also relates to an article obtained by welding a structure with such a layer C to itself or to another structure having an outer layer with the same composition as this layer C.

In addition, the weld of such a layer C can be adjusted so as to be very firm (permanent) or, on the contrary, to be easily peelable. A weld is said to be easily peelable according to this preferred alternative form of the present invention if the peel strength, determined according to ASTM Standard F88, is less than 3000 N/m, preferably less than 2000 N/m. This peel strength is advantageously greater than 300 N/m, indeed even greater than 600 N/m. The structures according to this advantageous alternative form exhibit, in addition, the advantage that the peel strength of the welds does not vary to any great extent from one welded item to another, in particular after sterilization of these items at 121° C. for at least 10 min. It can prove to be advantageous to use the structures according to this alternative form of the present invention in the manufacture of hermetic containers (that is to say, comprising one or more welds or other permanent fastenings which render them leaktight and therefore allow them to comprise fluids) separated into at least two compartments by an easily peelable weld.

Consequently, the present invention also relates to a hermetic container obtained from an article as described above which comprises at least one permanent weld and which is separated into at least two compartments by an easily peelable weld.

Such a container can be used, for example, to comprise fluids which have to be stored and/or sterilized separately and mixed before use by breaking the easily peelable weld. Examples of such fluids are glucose and certain vitamins and/or amino acids, and sodium bicarbonate solutions and certain acidic solutions.

Consequently, the present invention also relates to the use of such hermetic containers for the storage of fluids to be retained and/or sterilized separately and to be mixed immediately before use by breaking the easily peelable weld.

For the preparation of such multi-compartment hermetic containers, the welding temperatures are chosen according to the materials of the structure which is formed from them. The temperature chosen for the formation of the easily peelable weld is lower than that for the formation of the permanent weld by at least 5° C.

Consequently, the present invention also relates to a process for the manufacture of such a hermetic container where the formation of the easily peelable weld is carried out at a temperature lower than that for the formation of the permanent weld by at least 5° C.

The temperature at which the permanent weld is formed is advantageously chosen to be at least equal to 125° C., indeed even 130° C.; this temperature preferably does not exceed 160° C. or better still 150° C. The temperature at which the peelable weld is formed is advantageously at least 95° C., preferably at least 115° C.; it preferably does not exceed 140° C. or better still 130° C.

EXAMPLES

The following examples illustrate the invention without implied limitation.

Example 1

A film with a thickness of 200 µm was manufactured, by coextrusion, comprising three layers (A/B/C):

The layer A, with a thickness of 60 µm, was composed of a propylene copolymer comprising approximately 5% of ethylene. (Eltex® P KS 409 form Solvay). Although the softening temperature (Vicat point) (Tv) of this copolymer mentioned by the manufacturer is approximately 123° C., the manufacturing process used in this example (comprising in particular a stage of drawing by a factor of 4, which takes place at 120° C., a stage of relaxation lasting 18 s, which takes place at approximately the same temperature, and a stage of sudden cooling to 15° C.) has made it possible for the film to exhibit a low crystallinity and a true softening temperature of approximately 110° C.

The layer B, with a thickness of 100 µm, was composed of 50% of the same copolymer (Eltex® P KS 409) and of 50% of a copolymer of ethylene and of 1-octene (comprising approximately 14% of octene) (Dex Exacts® 8201).

The layer C, with a thickness of 40 µm, was composed of a mixture of 70% of the same propylene copolymer as in the layer A (Eltex P KS 409), of 22.5% of SEBS (Kratone® G1657), of 5% of ethylene-vinyl acetate (EVA) copolymer and of 2.5% of ethylene-methyl acrylate (EMA) copolymer (the latter two polymers having melting temperatures of approximately 70° C.).

The structure thus obtained exhibited a haze of 3.1% and a modulus of elasticity of 170 MPa. In addition, bags of 220×130 mm prepared from this structure, filled with one liter of water at 4° C., withstood being dropped from 2 m onto a flat surface.

Comparative Example 1

A film with a thickness of 200 µm was manufactured, by coextrusion, comprising three layers (A/B/C):

The layer A, with a thickness of 15 µm, was composed of a propylene homopolymer (Eltex® P HV 424 from Solvay). The softening temperature (Vicat point) (Tv) of this copolymer mentioned by the manufacturer is approximately 156° C.

The layer B, with a thickness of 135 µm, was composed of 50% of the same copolymer (Eltex® P KS 409) as the layer B in Example 1 and of 50% of a copolymer of ethylene and of 1-octene (comprising approximately 14% of octene) (Dex Exact® 8201).

The layer C, with a thickness of 50 μm, was composed of a mixture of propylene copolymer (Eltex® P KS409) at 77.5%, and of SEBS (Kraton® G1657), at 22.5%.

The structure thus obtained exhibited a haze of 12.1% and a modulus of elasticity of 440 MPa. In addition, bags of 220×130 mm prepared from this structure, filled with one liter of water at 4° C., did not withstand being dropped from 1 m onto a flat surface.

Example 2

A film with a thickness of 200 μm, comprising four layers (A/B1/B2/C), was manufactured by coextrusion using the process described in Example 1.

The layer A, with a thickness of 74 μm, has the same composition as the layer A of Example 1. The layer B1, with a thickness of 14 μm, has the same composition as the layer C of Example 1. The layer B2, with a thickness of 90 μm, has the same composition as the layer B of Example 1. The layer C, with a thickness of 22 μm, has the same composition as the layer C of Example 1.

The structure thus obtained exhibited a haze of 5.6% and a modulus of elasticity of 155 MPa. In addition, bags of 220×130 mm prepared from this structure, filled with one liter of water at 4° C., withstood being dropped from 2 m onto a flat surface.

Example 3

A film with a thickness of 200 μm, comprising four layers (A/B1/B2/C), was manufactured by coextrusion using the process described in Example 1:

The layer A, with a thickness of 90 μm, has the same composition as the layer A of Example 1. The layer B1, with a thickness of 20 μm, has the same composition as the layer C of Example 1. The layer B2, with a thickness of 70 μm, was composed of 45% of the same copolymer (Eltex P KS409), of 40% of the propylene-ethylene copolymer Huntsman W204 (comprising approximately 6% of ethylene, exhibiting a very broad distribution of the molecular masses; Tm=148° C., Tv=80° C.) and of 15% of SEBS block copolymer (Kraton G1657). The layer C, with a thickness of 20 μm, has the same composition as the layer C of Example 1.

The structure thus obtained exhibited a haze of 4.2%, a modulus of elasticity of 154 MPa, a tensile strength/yield strength ratio of 2.8, a water vapour transmission coefficient of 3 g/m²/day and an embrittlement temperature of −19° C. In addition, bags of 220×130 mm prepared from this structure, filled with one liter of water at 4° C., withstood being dropped from 2 m onto a flat surface.

Example 4

A film with a thickness of 205 μm, comprising four layers (A/B1/B2/C) was manufactured by coextrusion using the process described in Example 1:

The layer A, with a thickness of 85 μm, has the same composition as the layer A of Example 1. The layer B1, with a thickness of 20 μm, has the same composition as the layer C of Example 1. The layer B2, with a thickness of 80 μm, is composed of a mixture of 56% of the same propylene copolymer as in the layer A (Eltex P KS409), of 11% of ethylene-butene copolymer Tafmer® A4085 (Tc=54° C.), of 11% of propylene-butene copolymer Tafmer XR107L (Tv=91° C.), of 11% of polybutene Tafmer BL 4000 (Tv=116° C.; Tm=125° C.) and of 11% of SEBS block copolymer (Kraton G 1657). The layer C, with a thickness of 20 μm, has the same composition as the layer C of Example 1.

The structure thus obtained exhibited a haze of 2.8%, a modulus of elasticity of 165 PMa, a tensile strength/yield strength ratio of 2.3 and an embrittlement temperature of −15° C.

Example 5

The manufacture was carried out of a structure as set out in Example 3, except for the difference that the layer A was composed of 60% of propylene-ethylene copolymer comprising approximately 3% of ethylene (Eltex P KL104 from Solvay) (Tv=114° C.) and of 40% of poly(1-butene) (Tafmer BL 4000).

The structure thus obtained exhibited a haze of 2.3% and a modulus of elasticity of 155 MPa and made possible the manufacture of bags which, filled with one liter of water, withstood being dropped from 2 m.

Example 6

The manufacture was carried out of a structure as set out in Example 5, except for the difference that the layer A was composed of 75% of copolymer Eltex P KL104 and of 25% of propylene-1-butene copolymer comprising more than 10% of butene (Tafmer XR107L).

The structure thus obtained exhibited a haze of 2.8% and a modulus of elasticity of 150 MPa and made it possible to manufacture bags which, filled with one liter of water, withstood being dropped from 2 m.

Example 7

The manufacture was carried out of a structure as set out in Example 5, except for the difference that the layer A was composed of 65% of copolymer Eltex P KL104, of 25% of propylene homopolymer Eltex P HL402 and of 10% of SEBS block copolymer (Kraton G 1657).

The structure thus obtained exhibited a haze of 3.7% and a modulus of elasticity of 190 MPa and made it possible to manufacture bags which, filled with one liter of water, withstood being dropped from 2 m.

In comparison with the structure obtained in Example 5, this structure exhibits a reduced adhesion to a packaging based on polyolefins.

Example 8

A film with a thickness of 200 μm, comprising four layers (A/B1/B2/C), was manufactured by coextrusion. The layer A, with a thickness of 50 μm, was composed of 85% by weight of a mixture of polyolefins of controllable crystallinity and of 15% of SEBS block copolymer (Kraton G1657). The mixture of polyolefins of controllable crystallinity is composed of a propylene-ethylene copolymer comprising 4% of ethylene (KFC2004 from Borealis) and of a propylene-ethylene copolymer comprising approximately 3% of ethylene (Eltex® P KL104 from Solvay). The manufacturing process used in this example (comprising in particular a stage of drawing by a factor of 4, which takes place at 120° C., a stage of relaxation which lasts 18 s, which takes place at approximately the same temperature, and a stage of sudden cooling to 15° C.) has made it possible for the film to exhibit a low crystallinity and a true softening temperature of approximately 115° C. The layer B1, with a thickness of 60 μm, was composed of 100% of propylene-ethylene copolymer Huntsman W203. The layer B2, with a thickness of 70 μm, was composed of 50% of copolymer Eltex® P KL 104 and of 50% of propylene-ethylene copolymer Huntsman W209 (comprising approximately 5% of ethylene; Tm=120° C.; Tv<23° C.). The layer C, with a thickness of 20 μm, was composed of a mixture of 75% of copolymer Eltex® P KL104, of 22% of SEBS (Kraton® G1657), of 2% f ethylene-vinyl acetate (EVA) copolymer and of 1% of n ethylene-methyl acrylate (EMA) copolymer (the latter two polymers having melting temperatures of approximately 70° C.).

The structure thus obtained exhibited a haze of 3.9% and a modulus of elasticity of 175 MPa. In addition, bags of 220×130 mm prepared from this structure, filled with one liter of water at 4° C., withstood being dropped from 2 m onto a flat surface.

Example 9

Same structure as in Example 8, except that the layer C, with a thickness of 20 μm, was composed of a mixture of 78.5% of a propylene-ethylene copolymer (Eltex® P KL104), of 20% of SEBS (Kraton® G1657), of 1% of an ethylene-vinyl acetate (EVA) copolymer and of 0.5% of an ethylene-methyl acrylate (EMA) copolymer (the latter two copolymers having melting temperatures of approximately 70° C.).

Welding tests were carried out with the structures obtained in Examples 8 and 9. The results of these tests appear hereinbelow:

TABLE 1

Weldings with the structures according to Example 8: peel strength in N/m after sterilization at 121° C. for 30 min (results obtained according to ASTM F88)

| Welding T° (° C.) | Welding duration(s) | | | | | | | |
|---|---|---|---|---|---|---|---|---|
| | 0.2 | 0.4 | 0.6 | 0.8 | 1.0 | 1.2 | 1.4 | 1.6 |
| 145° C. | 3128 | | | | | | | |
| 136° C. | 3012 | 3343 | | | | | | |
| 134° C. | | | 3288 | | | | | |
| 132° C. | 970 | 1180 | 1280 | 1400 | | | | |
| 130° C. | | 831 | 1042 | 1295 | | | | 1498 |
| 128° C. | | | 1086 | | 1104 | | | |
| 126° C. | | 887 | | 940 | 1111 | | | |
| 124° C. | | 1124 | 1151 | | 1092 | 1101 | 946 | |
| 122° C. | | 951 | 1092 | | | | | 1189 |
| 120° C. | | | | | 1351 | | | 1140 |
| 118° C. | | | | 1218 | | | | |

TABLE 2

Peel strength (in N/m and according to ASTM F88) of a weld obtained at 125° C. and in 0.6 s

| Structure According to | Breakdown of the measurements Example 8 | Mean value Example 8 | Breakdown of the measurements Example 12 | Mean value Example 12 |
|---|---|---|---|---|
| Before sterilization | 425 | 495 | 311 | 308 |
| | 435 | | 285 | |
| | 557 | | 340 | |
| | 543 | | 356 | |
| | 515 | | 248 | |
| Sterilization at 121° C. for 10 min | 1042 | 970 | 624 | 604 |
| | 898 | | 584 | |
| Sterilization at 121° C. for 30 min | 1104 | 1226 | 705 | 677 |
| | 1235 | | 735 | |
| | 1274 | | 692 | |
| | 1346 | | 612 | |
| | 1171 | | 642 | |
| Sterilization at 121° C. for 60 min | 901 | 981 | 643 | 680 |
| | 1060 | | 718 | |
| Sterilization at 125° C. for 30 min | 1513 | 1533 | 940 | 927 |
| | 1390 | | 882 | |
| | 1611 | | 960 | |
| | 1688 | | 1002 | |
| | 1462 | | 852 | |

What is claimed is:

1. A multilayer structure composed of thermoplastic polymers, the structure not exceeding 0.1%, by weight of the total structure, of vinyl chloride polymers and of plasticizers having less than a molecular mass of 1000, said multilayer structure including at least three layers and comprising:
a first layer comprising at least 60%, by weight of the total first layer weight, of at least one polyolefin of controllable crystallinity defined as comprising at least 90% by weight of the total weight of said at least one polyolefin, of a compound selected from the group consisting of ethylene, propylene and butene, and having a softening temperature of less than 121° C., the first layer having a thickness at least 20% of total thickness of the multilayer structure and the first layer having a modulus of elasticity of less than 350 MPa;
a second layer, positioned between the first layer and a third layer, the second layer comprising at least 40%, by weight of the total weight of said second layer, of at least one polyolefin of controllable crystallinity, and having an overall softening temperature of less than 121° C.;
the third layer comprising at least 50%, by weight of the total weight of said third layer, of at least one polyolefin of controllable crystallinity, and having a thickness of from 5 to 30% of the total thickness of the structure and the third layer having a modulus of elasticity which is less than the modulus of elasticity of the first layer, said third layer being a sealing layer, where, taken as a whole, said third layer exhibits a melting temperature of greater than 121° C. and said third layer comprises at least one polymer having a melting temperature less than 121° C.

2. The multilayer structure according to claim 1, wherein the polyolefin of controllable crystallinity is a copolymer.

3. The multilayer structure according to claim 1, wherein the polyolefin of controllable crystallinity is a copolymer comprising at least 90%, by weight of the total copolymer weight, of a compound selected from the group consisting of ethylene, propylene and butene, and less than 10%, by weight of the total copolymer weight, of one or more other comonomers selected from the group consisting of $C_5$ to $C_{10}$ alkenes and carboxylic acids and esters.

4. The multilayer structure according to claim 1, wherein the first layer, taken as a whole, exhibits a melting temperature of greater than 121° C.

5. The multilayer structure according to claim 1, wherein constituent polymers of the first layer are selected exclusively from the group consisting of polyolefins of controllable crystallinity and of not very crystalline or amorphous polyolefins.

6. The multilayer structure according to claim 1, further comprising one or more outer layers composed of one or more thermoplastic polymers and disposed on the first layer or the third layer on a side opposite the second layer.

7. The multilayer structure according to claim 1, wherein a surface layer on the first layer comprises at least one of cycloolefin copolymers or PP homopolymer, mixed with SEBS.

8. The multilayer structure according to claim 1, wherein a surface layer on the first layer comprises cycloolefin copolymers as a mixture with SEBS and VLDPE.

9. The multilayer structure according to claim 1, wherein the structure has a haze/thickness ratio of less than 10%/200 μm.

10. An article obtained from the multilayer structure according to claim 1, said article comprising one of a tube, a film or a container.

11. An article formed by welding the structure according to claim 1 to itself or to another structure having an outer layer with the same composition as the third layer.

12. A hermetic container obtained from the article according to claim 11 comprising at least one permanent weld and separated into at least two compartments by an easily peelable weld.

13. A method of storing fluids to be retained and/or sterilized separately and to be mixed immediately before use comprising sealing said fluids in the hermetic container according to claim 12.

14. A method of manufacturing a container according to claim 12, comprising forming the easily peelable weld at a temperature at least 5° C. lower than a temperature for formation of a permanent weld.

15. The method according to claim 14, wherein the formation of the permanent weld is carried out at a temperature of between 125 and 160° C. and the formation of the easily peelable weld is carried out at a temperature of between 95 and 140° C.

16. A multilayer structure comprising:
    at least three layers comprising thermoplastic polymers and having no greater than 0.1% by weight of the total weight of the three layers, of vinyl chloride polymers and of plasticizers of a molecular mass less than 1000, forming a structure having a total thickness of between 100 and 400 μm, said structure simultaneously exhibiting:

a modulus of elasticity of less than 350 MPa,
    an amount of compounds which can be extracted with boiling hexane of less than 5%, and
    a haze/thickness ratio of less than 6%/200 μm.

17. A method of manufacturing a multilayer structure based on thermoplastic polymers and not exceeding 0.1%, by weight of the weight of the total multilayer structure, of vinyl chloride polymers and of plasticizers of a molecular mass less than 1000 and comprising at least 3 layers, said method comprising:

providing a first layer comprising at least 60%, by weight of the total weight of said first layer, of at least one polyolefin of controllable crystallinity defined as comprising at least 90%, by weight of the total weight of the at least one polyolefin, of a compound selected from the group consisting of ethylene, propylene and butene and as having a softening temperature of less than 121° C., thickness of the first layer being at least 20% of a total thickness of the structure and the first layer having a modulus of elasticity of less than 350 MPa;

providing a second layer, positioned between the first layer and a third layer, comprising at least 40%, by weight of the total weight of said second layer, of at least one polyolefin of controllable crystallinity, the second layer having an overall softening temperature of less than 121° C.;

providing the third layer comprising at least 50%, by weight of the weight of said third layer, of at least one polyolefin of controllable crystallinity, the thickness of the third layer being from 5 to 30% of the total thickness of the structure and the third layer having a modulus of elasticity less than the modulus of elasticity of the first layer;

co-extruding the three layers; and subjecting the co-extruding layers to at least one stage of drawing by at least 100% at a temperature between the maximum crystallization temperature of the polyolefins of controllable crystallinity (Tc) and Tm+15° C., wherein Tm denotes minimum melting temperature of the polyolefins, to at least one stage of relaxation at constant dimensions lasting at least 10 s in the same temperature range, and then to a stage of sudden cooling to a temperature of less than the maximum crystallization temperature Tc.

* * * * *